United States Patent [19]

Pohndorf et al.

[11] Patent Number: 5,441,504
[45] Date of Patent: Aug. 15, 1995

[54] SPLITTABLE LEAD INTRODUCER WITH MECHANICAL OPENING VALVE

[75] Inventors: Peter J. Pohndorf, Stillwater; Corinne A. Greene, Roseville; Linda L. Lach, Fridley, all of Minn.

[73] Assignee: Medtronic, Inc., Minneapolis, Minn.

[21] Appl. No.: 157,751

[22] Filed: Nov. 23, 1993

Related U.S. Application Data

[63] Continuation-in-part of Ser. No. 865,578, Apr. 9, 1992, abandoned.

[51] Int. Cl.[6] ............................................. A61M 29/00
[52] U.S. Cl. .................................... 606/129; 604/167; 606/191
[58] Field of Search ............. 606/129, 185, 191, 198; 604/164, 165, 167, 161; 128/642, 772; 607/116, 119, 122

[56] References Cited

U.S. PATENT DOCUMENTS

| 3,653,388 | 4/1972 | Tenckhoff . | |
|---|---|---|---|
| 3,844,292 | 10/1974 | Bolduc . | |
| 4,147,165 | 4/1979 | Tauschinski . | |
| 4,166,469 | 9/1979 | Littleford . | |
| 4,243,050 | 1/1981 | Littleford . | |
| 4,306,562 | 12/1981 | Osborne . | |
| 4,345,606 | 8/1982 | Littleford . | |
| 4,411,654 | 10/1983 | Boarini et al. | 604/165 |
| 4,512,351 | 4/1985 | Pohndorf . | |
| 4,581,025 | 4/1986 | Timmermans | 604/264 |
| 4,596,559 | 6/1986 | Fleischhacker | 604/170 |
| 4,687,469 | 8/1987 | Osypka | 604/161 |
| 4,772,266 | 9/1988 | Groshong | 604/164 |
| 4,921,479 | 5/1990 | Grayzel | 604/53 |
| 4,960,412 | 10/1990 | Fink | 604/167 |
| 4,973,312 | 11/1990 | Andrew | 604/158 |
| 4,997,424 | 3/1991 | Little | 604/161 X |
| 5,064,414 | 11/1991 | Revane | 604/165 |
| 5,098,392 | 3/1992 | Fleischhacker et al. | 604/165 |
| 5,098,393 | 3/1992 | Amplatz et al. | 604/167 |
| 5,108,374 | 4/1992 | Lemieux | 604/164 |
| 5,125,904 | 6/1992 | Lee | 604/164 |
| 5,147,316 | 9/1992 | Castillenti | 604/164 |
| 5,180,372 | 1/1993 | Vegoe et al. | 604/161 |
| 5,224,930 | 7/1993 | Spaeth et al. | 604/164 X |

FOREIGN PATENT DOCUMENTS 3140915 5/1982 Germany ............ A61M 5/14

Primary Examiner—Lee S. Cohen
Assistant Examiner—Jeffrey R. Jastrzab
Attorney, Agent, or Firm—Michael J. Jaro; Harold R. Patton

[57] ABSTRACT

A transvenous lead introducer having a mechanical valve assembly disposed thereon. In a preferred embodiment, a longitudinally splittable introducer sheath is provided with a sliding valve at or near one end. The sliding valve may be spring-biased to a normally closed position. A semicircular notch may be provided in the forward end of the sliding valve, so that the sheath may be effectively sealed even when a guide wire runs through the sheath. In an alternative embodiment, the sliding valve is adapted to have its forward end inserted into a notch in the cylindrical sheath body. The mechanical valve assembly is further configured to permit use with a splittable lead introducer sheath.

16 Claims, 13 Drawing Sheets

SPLITTABLE LEAD INTRODUCER WITH MECHANICAL OPENING VALVE

This is a continuation-in-part of copending application Ser. No. 07/865,578 filed Apr. 9, 1992.

FIELD OF THE INVENTION

This invention relates generally to the medical arts, and more particularly relates to an instrument for facilitating the introduction of transvenous leads into the human body.

BACKGROUND OF THE INVENTION

The use of electrically conductive transvenous leads, particularly cardiac pacing leads, is well known in the medical field. Many different methods and tools have been proposed in the prior art for allowing such leads to be introduced into the patient's subclavian vein via a relatively small incision. Often, medical device manufacturers may provide an introducer set to be used by doctors in implanting pacing leads.

In U.S. Pat. No. 4,147,165 issued to Tauschinski on Apr. 3, 1979 and entitled "Separable Needle for Inserting a Catheter Into the Blood Stream" there is disclosed a separable metallic needle having an inner plastic sealing tube for preventing leakage of the needle during insertion into the patient's blood vessel. After the needle is inserted, the inner sealing tube is removed. Thereafter, a lead is inserted through the needle into the blood vessel, and the separable needle is removed.

In the U.S. Pat. No. 4,166,469 issued to Littleford on Sep. 4, 1979 and entitled "Apparatus and Method for Inserting an Electrode" there are described several different techniques for the introduction of a transvenous pacing lead. One technique involves first puncturing the skin into an internal blood vessel such as the subclavian vein. One end of a guide wire is inserted into the vein by passing the guide wire through the lumen of the needle, after which the needle is then removed leaving the guide wire in place. Next, an introducer and introducer sleeve or sheath are slid along the guide wire to enter the vein, and the introducer and guide wire are removed, leaving the introducer sleeve in place. The introducer sleeve has sufficient diameter to allow a pacing lead to then be inserted therein and fed into the subclavian vein. The introducer cannot be slid back along the lead as the needle was retracted over the guide wire, since the pacemaker lead has a connector coupling disposed on its end that cannot pass through the introducer sleeve. Accordingly, the introducer sleeve is longitudinally scored or otherwise adapted to be longitudinally severed once the pacing lead has been positioned.

This first technique is also described in U.S. Pat. No. 4,243,050 issued to Littleford on Jan. 6, 1981 and entitled "Method for Inserting Pacemaker Electrodes and the Like"; in U.S. Pat. No. 4,306,562 issued to Osborne on Dec. 22, 1981 and entitled "Tear Apart Cannula"; in U.S. Pat. Nos. 4,346,606, 4,345,606 to Littleford on Aug. 24, 1982 and entitled "Split-Sleeve Introducers for Pacemaker Electrodes and the Like"; in U.S. Pat. No. 4,411,654 issued to Boarini et al. on Oct. 25, 1983 and entitled "Peelable Catheter With Securing Ring and Suture Sleeve"; in U.S. Pat. No. 4,581,025 issued to Timmermans on Apr. 8, 1986 and entitled "Sheath"; in U.S. Pat. No. 4,596,559 issued to Fleischhacker on Jun. 24, 1986 and entitled "Break-Away Handle for Catheter Introducer Set"; and in U.S. Pat. No. 4,687,469 issued to Osypka on Aug. 18, 1987 and entitled "Device for Slitting Introducers For Pacemaker Electrodes".

A second technique described in the Littleford '469 reference involves a necessarily larger diameter needle that is inserted into the subclavian vein. An introducer sleeve may then be inserted within the internal passage or lumen of the needle and into the vein, and the needle withdrawn over the introducer. In this second technique, the introducer sleeve is similarly adapted to be longitudinally severed once the pacing lead has been positioned.

In a third technique described in the Littleford '469 reference, the inner diameter of introducer sleeve is sized to closely receive the outer surface of the needle, so that the needle and sleeve may be inserted into the vein simultaneously, and the needle then withdrawn.

A common feature of any method for introducing a lead into a patient's blood vessel is that a hollow, tubular instrument is required to provide a temporary passage or conduit into the blood vessel, through which the lead may be slid to enter the blood vessel. Such a conduit also allows blood to escape from the blood vessel, and may allow air to enter the blood stream, possibly leading to embolic complications.

In addition to the potential adverse clinical effects of leakage of blood and air through an introducer sheath, the flow of blood out of an introducer sheath is likely to make the physician's task more difficult, and may encourage the physician to perform the introduction procedure more hastily. This, in turn, can increase the tension associated with the introduction procedure, and the risk that mistakes will be made.

In the prior art, it is commonly suggested that the physician can prevent (or at least restrict) the flow of blood out of a introducer sleeve while the pacing lead is being prepared for introduction into the vein by placing his or her thumb over the exposed end of the introducer sleeve. This suggestion is made, for example, in the above-noted Littleford '050, Littleford '606, Timmermans '025, and Fleischhacker '559 patents. A similar "solution" to the leakage problem that is sometimes practiced in the art is to squeeze or pinch the exposed end of the introducer sleeve between the thumb and forefinger.

Neither of these methods for reducing the undesired flow of fluids and air through the introducer sleeve is deemed by the inventors to be entirely acceptable. In both cases, at least one of the physician's hands is required, thereby making it difficult for the physician to attend to other or more important matters. Moreover, squeezing the exposed end of the introducer sheath can deform or even break the introducer at that point, making lead insertion difficult and increasing the danger of damage to the lead as it passes through the introducer.

In addition, neither placing the thumb over end of the introducer, nor squeezing the end of the introducer, will be sufficiently effective in preventing the flow of blood and air in the introducer once a guide wire has been threaded through the introducer. Also, the configuration of the end of some types of introducer sheaths is such that it is difficult or impossible to seal the end of the introducer shut with the thumb.

A tricuspid valve system for catheter (as opposed to lead) introducers is also deemed to be unacceptable for use in conjunction with lead introducers. The tricuspid valve arrangement for catheters could damage the sensitive lead tip of a pacing lead. The application of pressure required to open the tricuspid value can result in distortion or breakage of the lead tip. Moreover, some presently known tricuspid systems are lubricated with silicone-based oil. The electrical properties of pacing/sensing leads, and the chemical properties of steroid-eluting lead tips and the like, can be severely effected by coming in contact with the oil.

It is believed by the inventors, therefore, that there is presently a need for a method and apparatus for preventing the undesired flow of air and blood in an introducer sheath prior to the insertion of a cardiac pacing or sensing lead.

SUMMARY OF THE INVENTION

In accordance with the present invention, an introducer sheath for implanting transvenous cardiac pacing and sensing leads is provided in which the flow of blood and air is significantly reduced without requiring a physician or surgical assistant to maintain constant pressure on the end of the introducer sheath. Also in accordance with the present invention, the means for preventing blood and air flow through the introducer sheath does not impair the sheath's ability to accept a lead therein, and which does not increase the risk of damage to the lead as it is being introduced into the patient.

Further in accordance with the present invention, there is provided a means for allowing the physician to quickly, simply, safely and repeatedly effect a temporary seal over the introducer sheath, prior to insertion or reinsertion of the lead.

In one disclosed embodiment of the invention, an introducer sheath of the type that is longitudinally splittable is provided with a mechanical opening valve disposed on or near its proximal end. The valve is operable to slide into place over the proximal end of the introducer sheath after the vessel dilator and guide wire have been withdrawn, such that the flow of blood and air through the sheath is prevented.

In another embodiment, the sliding valve is provided with a semicircular notch on its forward end, so that the valve may be closed around a guide wire if the guide wire is left in the vein, such as during a multiple lead implantation procedure.

In another embodiment of the invention, the sliding valve is provided with a horizontal groove on its forward edge, in addition to the guide wire notch. The horizontal groove is adapted to engage a complementary collar disposed around the circumference of a vessel dilator's proximal endpiece, so that the introducer sheath and vessel dilator remain stationary with respect to one another as the introducer is inserted into the blood vessel. When the sliding valve is pulled back and the vessel dilator withdrawn, the valve may then be closed as in the first embodiment.

In still another embodiment of the invention, the sliding valve is provided with a spring element disposed on its underside, the spring element tending to keep the valve in a closed position over the top of the introducer sheath unless the valve is pulled back.

In yet another embodiment of the invention, the sliding valve is housed within a housing disposed at some point along the length of the introducer sheath where a notch is provided to receive the forward end of the sliding valve.

In another embodiment of the invention, a unitary housing is provided at the proximal end of the introducer sheath. Protruding from opposite sides of the housing are spring compression elements which normally obstruct or seal the end of the sheath, but which, when depressed as by squeezing between the thumb and forefinger, expose the end of the sheath.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF SPECIFIC EMBODIMENTS OF THE INVENTION

It is to be understood, that the present invention is not limited to use only in introducing atrial or ventricular pacing leads, and may be employed in introducing many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, the present invention may be employed in introducing many of various types of therapeutic or diagnostic catheters and is not limited only to the introduction of electrical leads. For purposes of illustration only, however, the present invention is below described in the context of the introduction of endocardial pacing leads.

Figure 1:
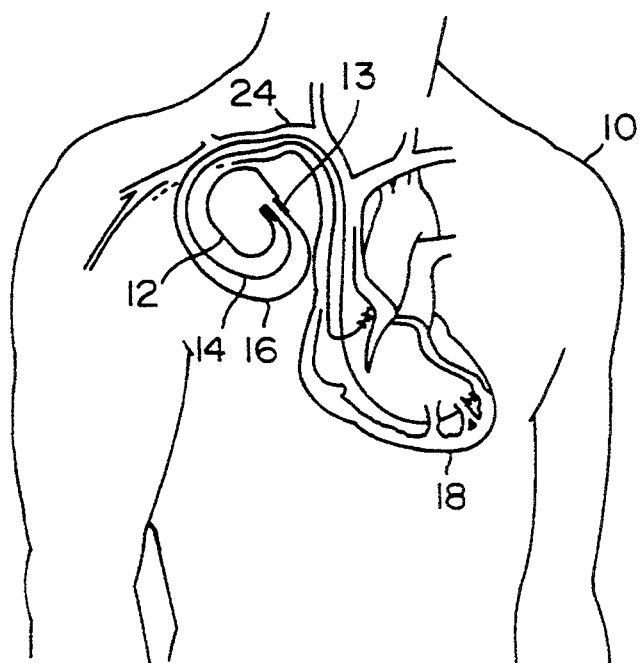
FIG. 1 is diagram illustrating the placement of a pacemaker and pacing/sensing leads in a patient.

FIG. 1 depicts a typical arrangement of a pacing system implanted in a patient 10, the pacing system comprising a subcutaneously disposed pacemaker 12 and transvenous pacing/sensing leads such as 14 and 16. As seen leads 14, 16 have relatively bulky connectors 13 at proximal ends. In FIG. 1, the distal end of pacing lead 14 is shown disposed generally in the atrial region of the patient's heart 18, while the distal end of pacing lead 16 is disposed generally in the ventricular region of heart 18.

The preferred prior art method of lead introduction compatible with an introducer in accordance with the presently disclosed embodiment of the invention will be described with reference to FIGS. 2 through 14.

Figure 2:
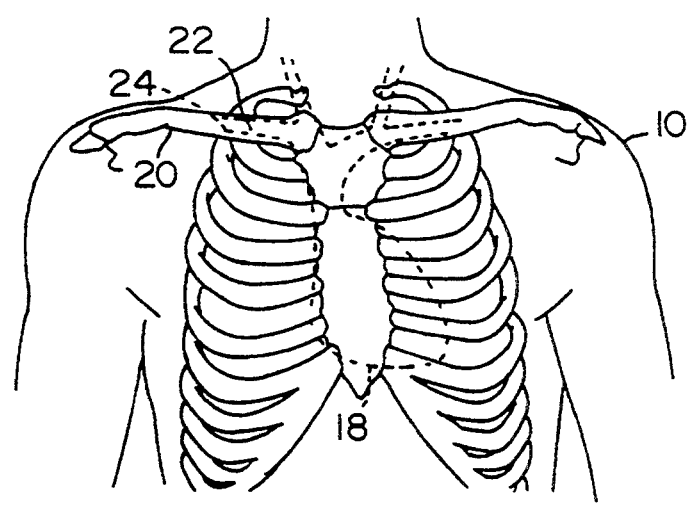
FIG. 2 is a diagram illustrating an appropriate entry site for implantation of a transvenous cardiac pacing/sensing lead.

Referring to FIG. 2, and in accordance with common practice in the medical arts, the entry site for a subclavian vein puncture is commonly chosen to be just below and slightly medial to the junction of the middle and inner third of the clavicle 20, at an area designated generally as 22 in FIG. 2. In FIG. 2, the patient's subclavian vein 24 and heart 18 are shown in phantom.

Figure 3:
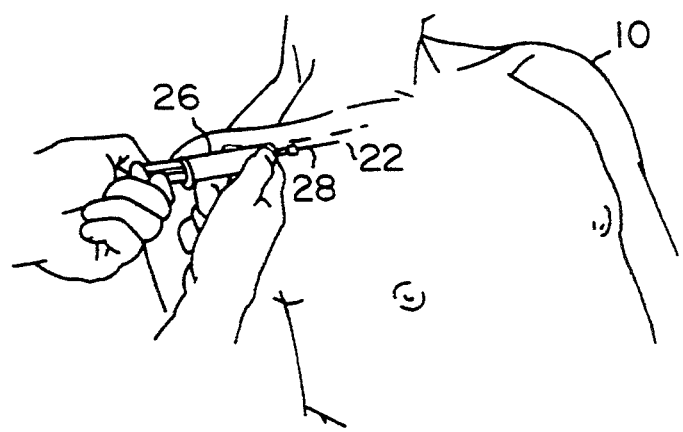
FIGS. 3 through 14 are diagrams illustrating successive stages of a prior art transvenous pacing/sensing lead introduction procedure.
Figure 4:
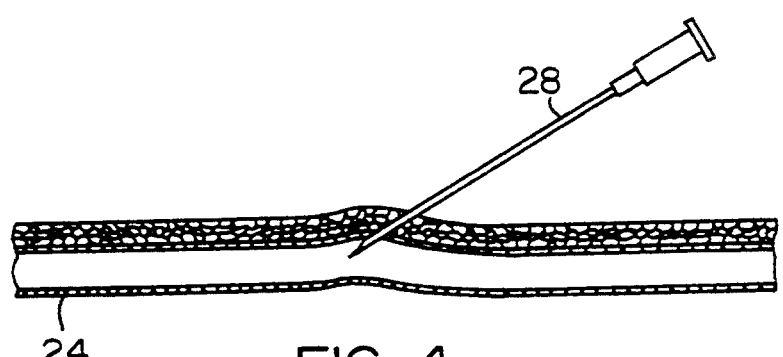

Turning to FIG. 3, the subclavian vein puncture is accomplished by the physician using a disposable syringe 26 having a thin-wall needle 28 detachably connected thereto. Aspiration is performed as the needle is advanced into the subclavian vein, to verify proper needle placement within vessel 24. Next, aspirating syringe 26 is disconnected from needle 28, which remains in vessel 24 as shown in FIG. 4. Typically, the physician will place his or her finger over the needle to avoid air aspiration and excessive bleeding.

Figure 5:
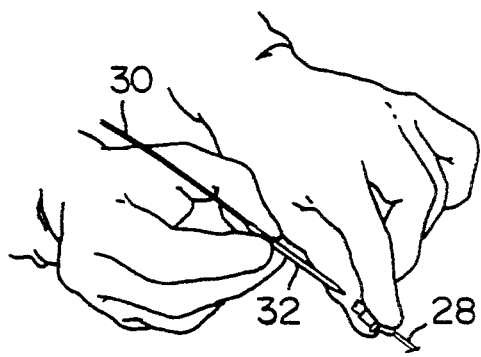
Figure 6:
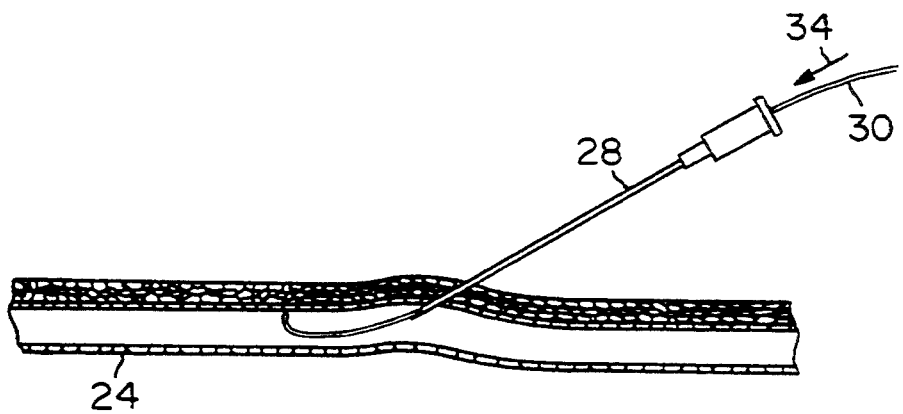
Figure 7:
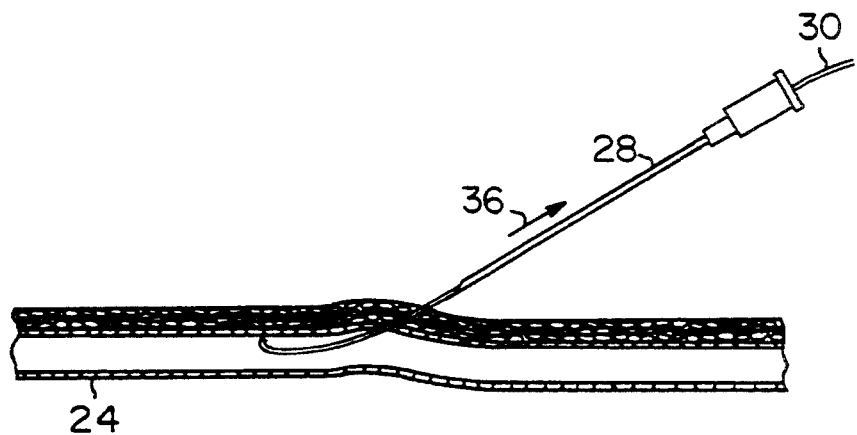

The next step in the lead implantation procedure involves insertion of a conventional J-type guide wire 30 through needle 28, as illustrated in FIG. 5. Typically, guide wire 30 is equipped with a tip deflector 32 for facilitating insertion of wire 30 into the lumen of needle 28. As shown in FIG. 6, as wire 30 is fed through needle 28 in the direction of arrow 34, the distal end of wire 30 exits the tip of needle 28, and wire 30 regains its "J" shape within vessel 24. Once wire 30 has entered vessel 24, needle 28 is withdrawn in the direction of arrow 36 in FIG. 7, leaving wire 30 in place. Wire 30 is advanced along vessel 24 until its distal end is disposed generally in the area of the patient's superior vena cava, leaving approximately 15 to 20-cm of the proximal end of wire 30 exposed.

Figure 8:
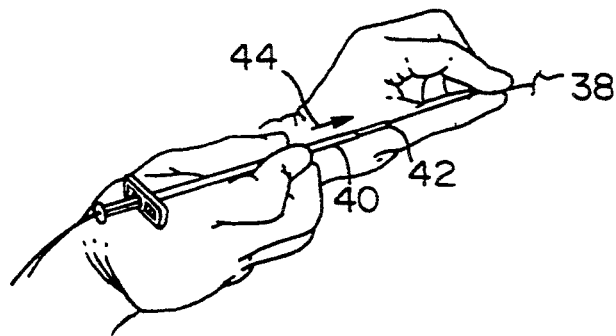
Figure 9:
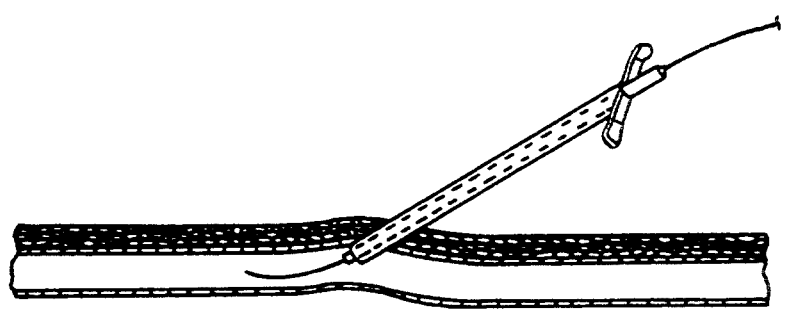

A small skin incision 38 is made at the guide wire entry site, parallel to the clavicle, as shown in FIG. 8. In the next stage of the implantation procedure, an introducer sheath 40 with tapered vessel dilator 42, as a unit, are threaded onto the proximal end of wire 30. Sheath 40 and dilator 42 are advanced in the direction of arrow 44, through the subclavian fascia and into the subclavian vein 24, until a short length (e.g., 2 to 8-cm) of sheath 40 and vessel dilator 42 remain exposed, as shown in FIG. 9.

Figure 10:
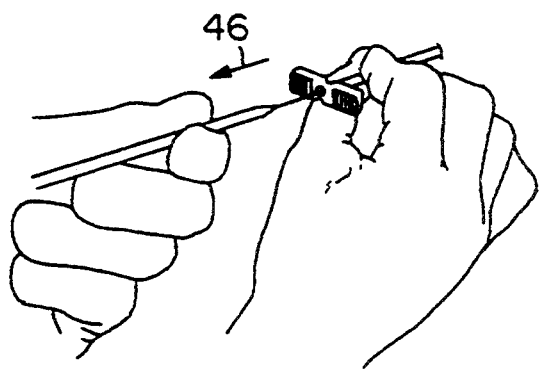
Figure 11:
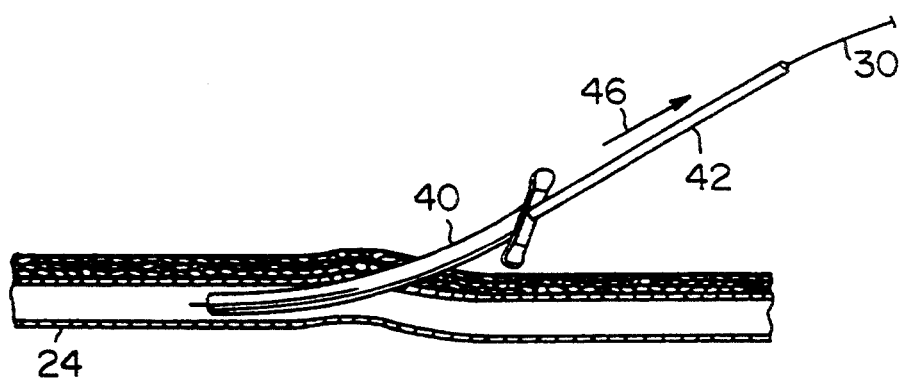

Next, as shown in FIGS. 10 and 11, vessel dilator 42 is withdrawn in the direction of arrow 46, leaving introducer sheath 40 and guide wire 30 in place with its distal end disposed within subclavian vein 24. Guide wire 30 may be removed at this point as well, although it may be left in place in case the lead needs to be repositioned or reinserted. As shown in FIG. 11, introducer sheath 40 would provide an unobstructed conduit for blood to exit subclavian vein 24, and at the stage of lead implantation depicted in FIG. 11, blood could be allowed to escape. In the prior art, as previously noted, it has been suggested that the escape of blood and air aspiration at this stage of the implantation procedure may be reduced by placing a thumb over the proximal end of introducer sheath 40, or by squeezing the proximal end of sheath 40.

Figure 12:
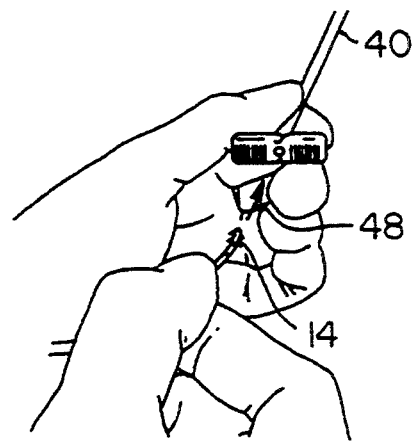
Figure 13:
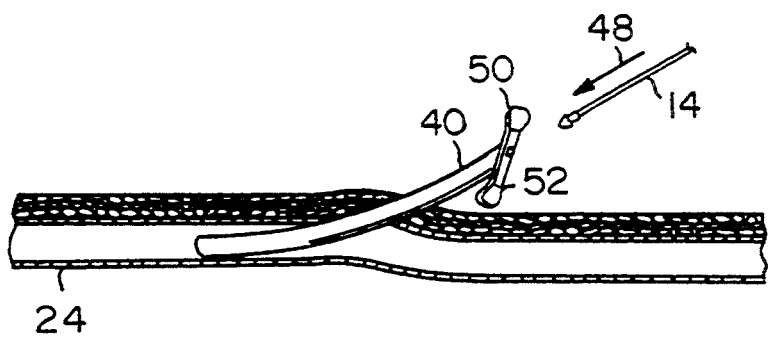
Figure 14:
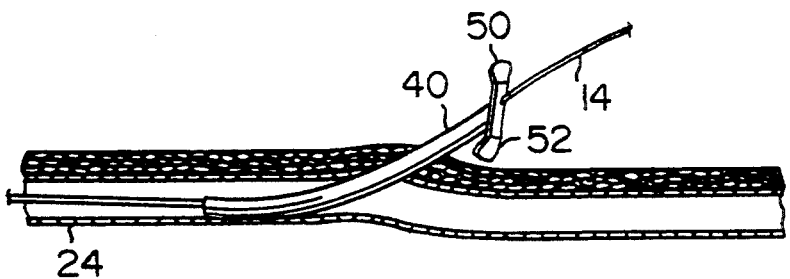

In the final stages of the lead implantation procedure, illustrated in FIGS. 12 through 14, pacing lead 14 is inserted into the proximal end of introducer sheath 40 in the direction of arrow 48, and advanced into the desired position within patient 10.

Lastly, introducer sheath 40 is removed. Removal of introducer sheath 40 may be accomplished in one of several known ways, depending upon the particular type of introducer sheath 40. As mentioned previously, because a lead has a relatively bulky connector 13 at the proximal end, it is quite often not possible to remove the introducer from over the lead by passing the lead through the sheath. Connector 13 will not pass through. In such a circumstance it has become common to provide means for removing the sheath without having to pass it over an end of the lead. For example, as disclosed in the above-noted Osborne '562 patent, sheath 40 may be longitudinally split by pulling tabs 50 and 52. It is therefore desirable to provide a valve which may be split along with the sheath.

As shown in FIG. 1, pacemaker 12 may operate in conjunction with two pacing leads. In that case, as with single-lead implants, it may be necessary to keep guide wire 30 in place until after the first lead has been implanted. Thus, as previously noted with reference to FIGS. 10 and 11, guide wire 30 may be left in place when dilator 42 is withdrawn. The first lead, if it is sufficiently small, may be introduced into subclavian vein 24 alongside guide wire 30, and then the first introducer sheath is removed leaving guide wire 30 in place. Then, a second introducer sheath and vessel dilator can be guided along guide wire 30 in the same manner as the first, before guide wire 30 is finally removed.

As would be apparent to one of ordinary skill in the art, leaving guide wire 30 in place while the first lead is implanted further reduces the physician's ability to restrict bleeding and air aspiration through the first introducer sheath, since guide wire 30 will prevent either the physician's thumb or the squeezing of introducer sheath from tightly sealing the sheath.

Figure 15:
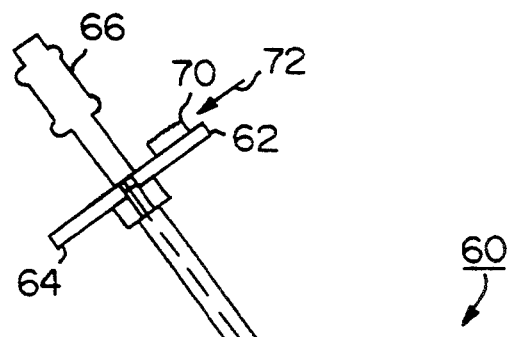
FIG. 15 is a diagram of a lead introducer in accordance with one embodiment of the present invention.

Turning now to FIG. 15, an introducer 60 in accordance with one embodiment of the present invention is illustrated. Introducer 60 comprises an introducer sheath 61 in which a vessel dilator 66 is inserted. A tapered end 68 of vessel dilator 66 facilitates the introduction of sheath 60 into the subclavian vessel. Thereafter, guide wire 30 and vessel dilator 66 are withdrawn from the patient. In the embodiment of FIG. 15, sheath 61 is of the type that is removed from a pacing lead by being longitudinally split apart. In particular, introducer sheath 61 is split apart by grasping tabs 62 and 64 as it is being withdrawn from the lead introduction site. Sheath 61 is constructed to either tear readily in a longitudinal direction (such as through use of a longitudinally oriented polymer), along line 86-1, or may be advantageously employed in conjunction with introducer sheaths that are removable by other means, such as by a sheath slitter or the like, as is commonly known in the art and discussed below.

As shown in FIG. 15, and in accordance with a primary aspect of the presently disclosed embodiment of the invention, a sliding mechanical valve 70 is disposed on tab 62 of introducer 60. As will be hereinafter described in greater detail, valve 70 is manually slidable in the direction of arrow 72 to substantially cover the circular opening at the end of sheath 61 between tabs 62 and 64. Tabs 62 and 64 are provided, in part, to permit mechanical valve 70 to be readily split apart and thereby permit introducer sheath 61 to also be split apart. In such a fashion mechanical valve 70 of the present invention may be provided on splittable lead introducer systems.

Figure 16:
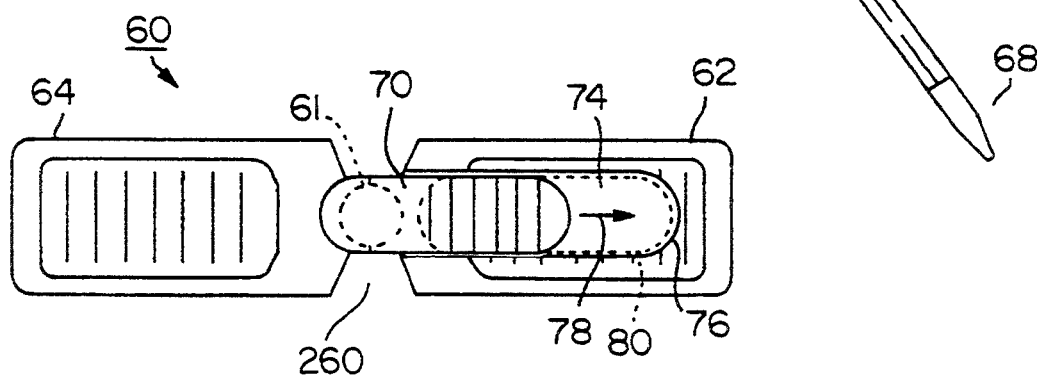
FIG. 16 is an enlarged top view of the introducer sheath of the introducer of FIG. 15.
Figure 20:
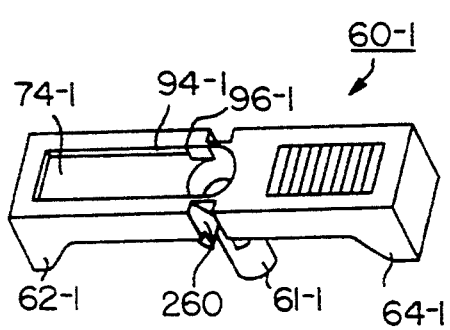
FIG. 20 is an enlarged perspective view of a portion of the introducer sheath of the introducer of FIG. 18.

Operation of mechanical valve 70 may be better appreciated with reference to FIG. 16, which is a greatly enlarged end view of introducer 60, looking down upon tabs 62 and 64, axially along the cylindrical body of sheath 61. Tabs 62 and 64 are integral, as best seen in FIG. 20, but are joined across gap 260 by only a relatively thin bridge of material. Through such a construction then tabs 62 and 64 may be split apart by hand to initiate splitting of mechanical valve 70 and sheath 61. In FIG. 16, vessel dilator 66 has been removed from sheath 61, and valve 70 is shown in a 'closed' position, such as to effectively cover and seal the top end of cylindrical sheath 61, the circular outline of which being designated by a dotted line in FIG. 16. In the embodiment of FIG. 16, valve 70 is inset within a shallow well 74 in the upper surface of tab 62, with well 74 having a curved end 76 substantially conforming to the shape of valve 70. Valve 70 may be slid in the direction of arrow 78, thereby uncovering the top end of cylindrical sheath 60. Valve 70 having been moved to the 'open' position is depicted by dotted outline 80 in FIG. 16.

Figure 17:
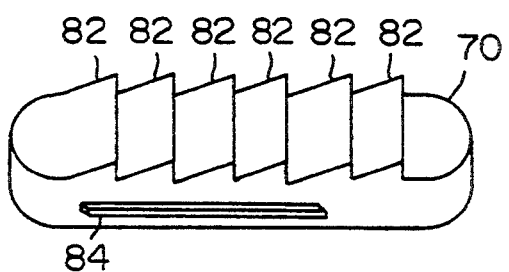
FIG. 17 is an enlarged perspective view of the sliding valve of the introducer sheath of FIGS. 15 and 16.

In FIG. 17, a greatly enlarged perspective view of sliding valve 70 is Shown. The top of valve 70 is provided with a series of sawtooth ridges 82, allowing the physician to easily slide valve 70 back and forth within well 74 with only slight downward pressure.

On each side of valve 70 is a horizontal track such as track 84 shown in FIG. 17. Tracks 84 are engaged in grooves of a conforming size disposed along the respective inner side walls of well 74. The grooves in the side walls of well 74 will be more readily discernible in later FIGS.

Figure 39:
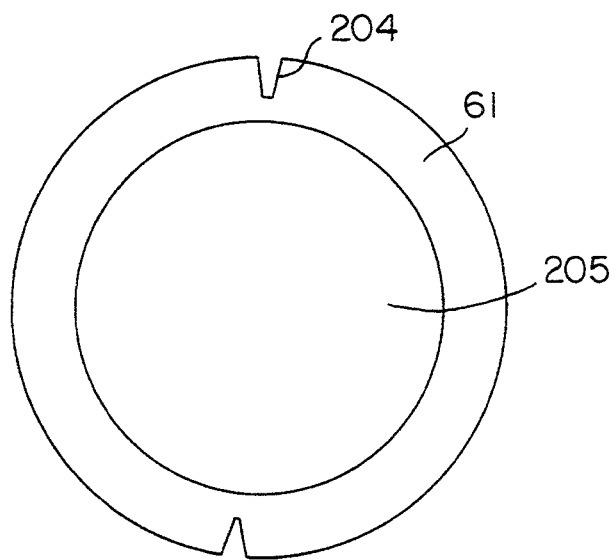
FIG. 39 is a cross sectional view of an introducer sheath having a score line to provide splittablility.
Figure 40:
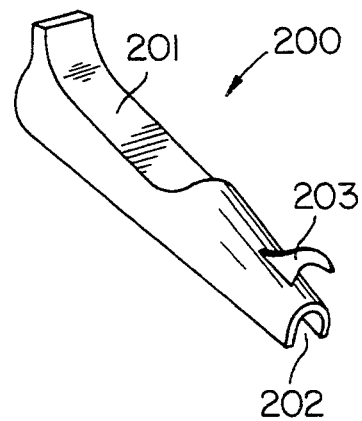
FIG. 40 is a view of a sheath slitter which may be used to split an introducer sheath constructed according to the present invention.

It should be appreciated that a desirable feature of the valve of the present invention is the ability to be used with a splittable sheath. Specifically, in the preferred embodiment of the present invention sheath 61 includes means for permitting removal of sheath 61 from a lead disposed therethrough without requiring sheath 61 to be removed from an end of the lead. Specifically sheath 61 may be removed from a pacing lead by being longitudinally split apart along line 86-1. In particular, introducer sheath 61 is split apart by grasping tabs 62, 64 and splitting them apart as described above, as sheath is being withdrawn from the lead introduction site. Various means may be used to provide a sheath 61 which may be split along line 86-1, these may include providing a score line 204 or groove along sheath 61 in the longitudinal direction as depicted in FIG. 39 and discussed, for example in U.S. Pat. No. 4,596,559 to Fleischacker; providing a sheath 61 manufactured from a material having a longitudinal orientation, such as an extruded TEFLON, which permits the sheath to be torn in a longitudinal direction, discussed for example in U.S. Pat. No. 4,306,562 to Osborne; providing a line of material weakened in a longitudinal direction, and specifically along line 86-1 as shown in Vegoe et al U.S. Pat. No. 5,180,372, incorporated herein by reference. Other sheaths may be used which are severable by means of a special slitter 200, as depicted in FIG. 40 which has handle 201, groove 202 shaped to conform to a pacing lead (not shown), and blade 203 to cut sheath 62 longitudinally and permit sheath 61 and valve assembly attached thereto to be removed from lead without requiring the introducer to be removed over an end of the lead. Further details of such a slitter may be found in the U.S. Pat. No. 4,687,469 to Osypka. Various other equivalent means may also be used to accomplish splitting sheath 61 along line 86-1.

It is contemplated by the inventors that in the above-described embodiment of the invention, as well as in later embodiments, the introducer sheath tabs can be made of polyethylene or any other suitably resilient and sterilizable material, although the use of a particular material is not deemed to be absolutely essential to the successful practice of the present invention. It is also believed that the introducer of the present and later embodiments of the invention can be readily adapted by a person of ordinary skill in the art to any of the various sizes of introducers commonly known and used.

One feature of the embodiment of the invention described above with reference to FIGS. 15 through 17, as well as of the embodiment to be hereinafter described with reference to FIGS. 18 through 25, is that the size and shape of the sliding valve may be chosen so that the same part can be used in the manufacture of introducers of various sizes; that is, the size of the valve and related components need not be customized for a particular size introducer sheath. In addition, it is contemplated by the inventors that the valves in introducers in accordance with any of the embodiments of the invention disclosed herein can be color-coded, such that a physician can identify the size of the introducer sheath by quick reference to the color of the valve.

Figure 18:
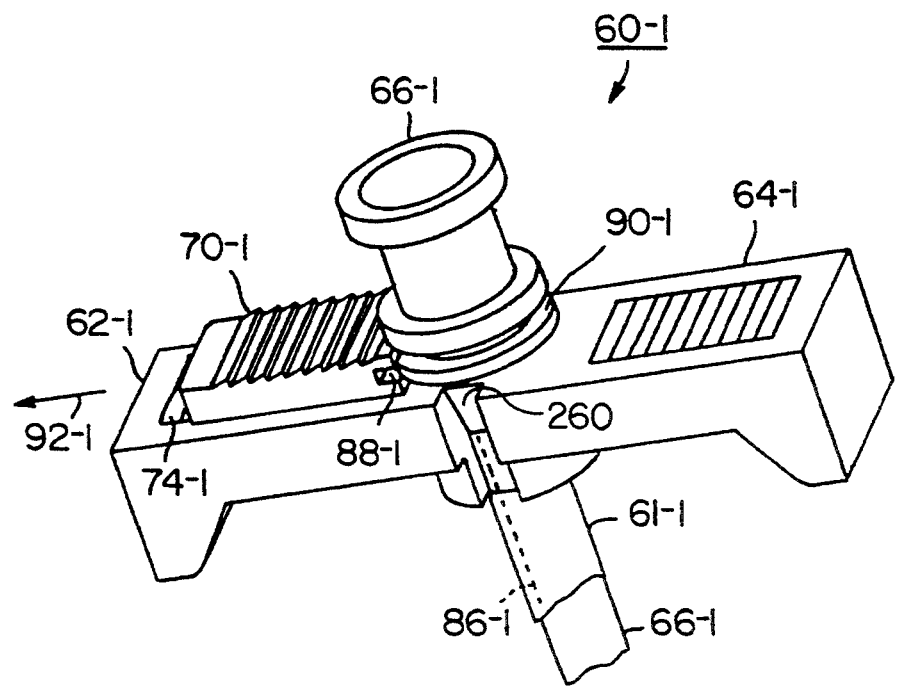
FIG. 18 is an enlarged perspective view of a lead introducer in accordance with another embodiment of the present invention.

Turning now to FIG. 18, a perspective view of a slightly different embodiment of the present invention is shown. In FIG. 18, the individual introducer components have retained the same reference numerals as those of the embodiment of FIGS. 15 through 17, but are followed by a "dash one" (-1) suffix.

In FIG. 18, introducer 60-1 is shown with a vessel dilator 66-1 inserted into sheath 61-1. As in the embodiment of FIGS. 15 through 17, introducer 60-1 is of the type in which sheath 61-1 is removed from around an implanted lead by grasping tabs 62-1 and 64-1 and pulling, causing sheath 61-1 to split longitudinally away from the lead, the line of the splitting being designated in FIG. 18 by a dotted line 86-1.

In the embodiment of FIG. 18, sliding valve 70-1 is provided with a groove 88-1 along one end which is capable of engaging an annular collar 90-1 disposed on the proximal end of vessel dilator 66-1. With this arrangement, vessel dilator 66-1 may be secured in place in sheath 61-1 and be prevented from sliding back out of sheath 61-1 as introducer 60-1 is inserted into the subclavian vein. The ability to lock dilator 66-1 is believed to be advantageous, since dilator 661 may be pushed out by venous pressure or venous anatomy, especially if there is low friction or a loose fit between dilator 66-1 and sheath 61-1. With the locking mechanism of the embodiment of FIG. 18, the physician need not be concerned with the relative positions of dilator 66-1 and sheath 61-1 as the introducer is being inserted. Once sheath 61-1 has been properly positioned within the subclavian vein, valve 70-1 may be slid back (in the direction of arrow 92-1 in FIG. 18), allowing vessel dilator 66-1 to be removed from sheath 61-1. Then, valve 70-1 can be slid into place such that it covers and seals the top of cylindrical sheath 61-1.

Figure 19:
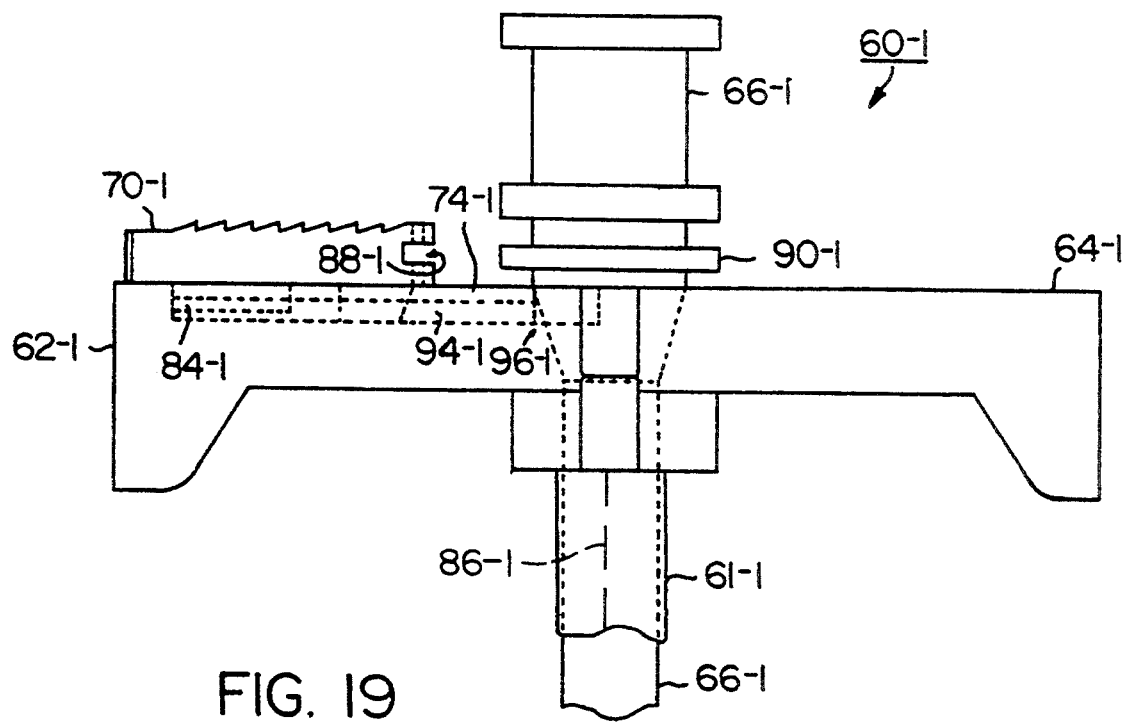
FIG. 19 is an enlarged perspective view of the lead introducer of FIG. 18.

In FIG. 19, a side view of introducer 60-1 from FIG. 18 is shown, wherein such features as groove 88-1 in sliding valve 70-1, and collar 90-1 of vessel dilator 66-1 are somewhat more apparent than in FIG. 19. As in the embodiment of the invention described with reference to FIGS. 15 through 17 above, sliding valve 70-1 is disposed within a well 74-1 in tab 62-1, and valve 70-1 is provided with horizontal tracks 84-1 which are received in conforming grooves, one of which is designated as 94-1 in FIG. 19, in the side walls of well 74-1. It is to be noted from FIG. 19 that grooves such as 94-1 need not extend the entire length of well 74-1, but instead may terminate at the point designated generally as 96-1 in FIG. 19. As a result, valve 70-1 is prevented from being separated from tab 62-1, even when sheath 61-1 is split apart. This is believed to be desirable from the standpoint of not allowing a small piece of introducer 60-1 to be lost during the surgical implantation procedure.

The extent of grooves 94-1 in the side walls of well 74-1 can be more readily appreciated with reference to FIG. 20, which is an enlarged perspective view of a portion of introducer 60-1, including tabs 62-1 and 64-1, but having sliding valve 70-1 removed. FIGS. 21, 22, 23, 24, and 25 are perspective, front, top, side, and bottom views, respectively, of sliding valve 70-1 from the embodiment of FIGS. 18 and 19.

Figure 21:
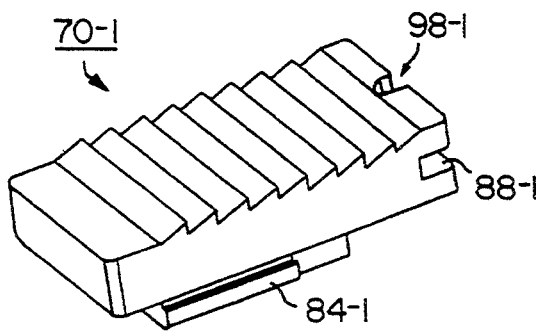
FIGS. 21 through 25 are perspective, front, top, side, and bottom views of the mechanical valve of the introducer of FIG. 18.
Figure 22:
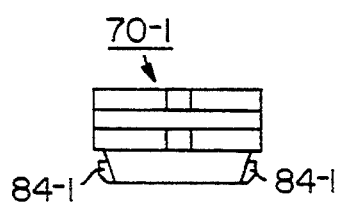
Figure 23:
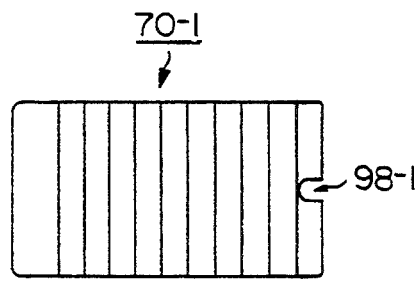
Figure 24:
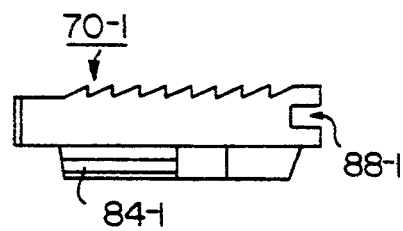
Figure 25:
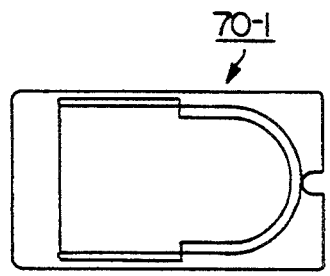

In FIGS. 21, 23, and 25, another feature of the presently disclosed embodiment of the present invention is shown, in particular, a semi-circular notch 98-1 disposed in the front edge of valve 70-1. Recall from the foregoing discussion of the lead implantation procedure that in the case that two leads are to be implanted during one procedure, it may be desirable to leave guide wire 30 in the subclavian vein while the first lead is introduced, so that the guide wire is available for guiding the introduction of a second introducer sheath and vessel dilator. In that case, the problems with blood leakage and air aspiration are further exacerbated by the fact that the guide wire reduces the effectiveness of placing a thumb over the top opening of the sheath or of pinching the sheath closed.

Semi-circular notch 98-1 in valve 70-1 is preferably the same size as guide wire 30, so that when valve 70-1 is slid into a closed position, guide wire 30 is received within notch 98-1, substantially completing the seal over the top of sheath 61-1. If no guide wire is present when valve 70-1 is closed, valve 70-1 is able to slide slightly further over the top of sheath 61-1, so that notch 98-1 is advanced slightly past the top of sheath 61-1.

Figure 26:
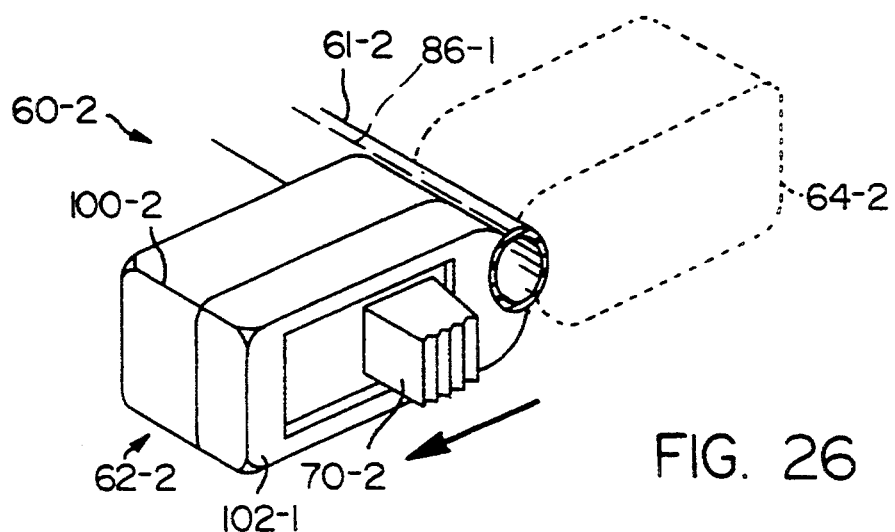
FIG. 26 is an enlarged perspective view of a lead introducer in accordance with another embodiment of the present invention.

Turning now to FIG. 26, a perspective view of another embodiment of the present invention is shown, the components thereof being designated by reference numerals followed by a "dash two" (-2) suffix. In the embodiment of FIG. 26, introducer 60-2 has a tab 62-2 disposed on the distal end of introducer sheath 61-2 contains a sliding mechanical valve 70-2. A second tab 64-2 is considered optional in this embodiment and is therefore shown in phantom in FIG. 26.

Figure 27:
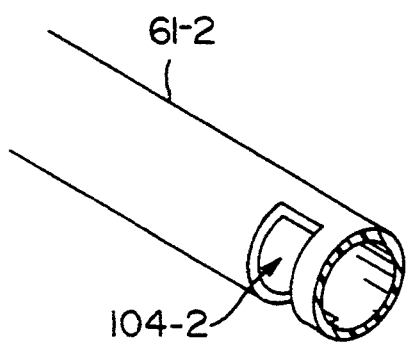
FIG. 27 is a perspective view of the sheath from the introducer of FIG. 26.
Figure 28:
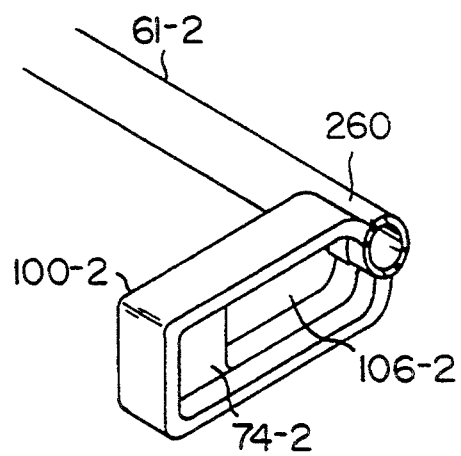
FIG. 28 is a perspective view of the sheath and valve housing from the introducer of FIG. 26.

Tab 62-2 in FIG. 26 comprises a housing 100-2 and housing cover 102-2. With reference now to FIGS. 27 through 34, various stages in the assembly of introducer 60-2 will be described. Assembly of introducer 60-2 begins by forming a notch 104-2 near the proximal end of cylindrical sheath body 61-2, as shown in FIG. 27. Next, housing 100-2 is fitted over notch 104-2, as shown in FIG. 28. Housing 100-2 defines a first shallow well 74-2 which receives sliding valve 70-2. Well 74-2, in turn, has a second, deeper well 106-2 disposed therein, for receiving a spring element on the underside of valve 70-2, to be hereinafter described with reference to FIGS. 32 through 34.

Figure 29:
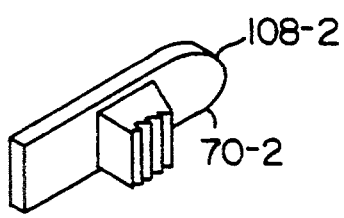
FIG. 29 is a perspective view of the valve from the introducer of FIG. 26.
Figure 30:
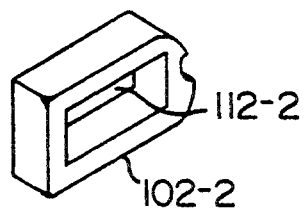
FIG. 30 is a perspective view of the housing cover from the introducer of FIG. 26.

As shown in FIG. 29, valve 70-2 has a forward end 108-2 which is curved to substantially conform to the inner wall of sheath 61-2. After valve 70-2 is fitted into well 74-2, housing cover 102-2, shown in FIG. 30, is secured, as by sonic bonding or the like, onto housing 100-2, resulting in the fully assembled tab 62-2 shown in FIG. 26.

Figure 31:
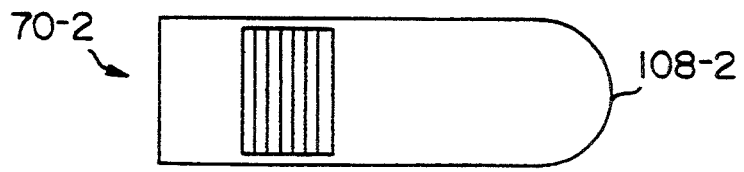
FIGS. 31, 32, and 33 are top, side, and bottom views, respectively, of the valve from the introducer of FIG. 26.
Figure 32:
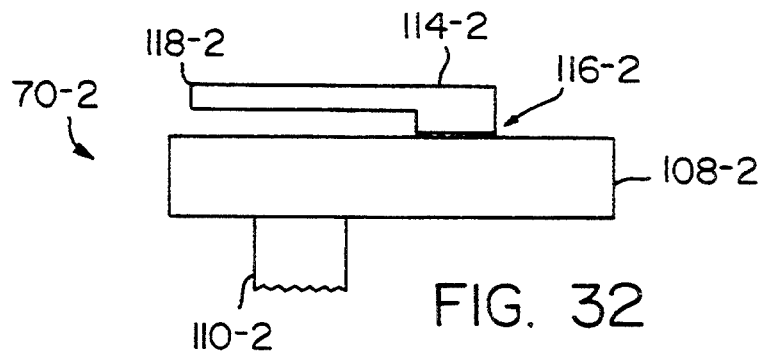
Figure 33:
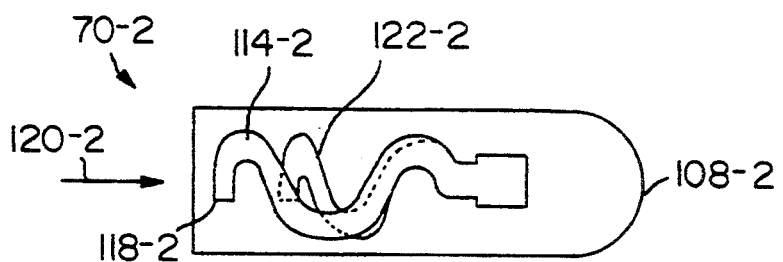

FIG. 31 is a top view of valve 70-2. FIG. 32 is a side view of valve 70-2. A ridged protrusion 110-2 extends through a rectangular hole 112-2 (see FIG. 30) disposed in housing cover 102-2. On the opposite face of valve 70-2, a spring element 114-2 is formed, being attached to valve 70-2 at a point designated generally as 116-2 and having an unattached end designated 118-2 in FIG. 32. The configuration of spring element 114-2 may be better appreciated with reference to FIG. 33. Spring element 114-2 is made of polyethylene or another suitably resilient material and has a substantially curved shape which is capable of being compressed in response to application of force directed on its unattached end 118-2 in the direction of arrow 120-2. Spring element 114-2 in a compressed state is illustrated by dotted line 122-2 in FIG. 33.

Figure 34:
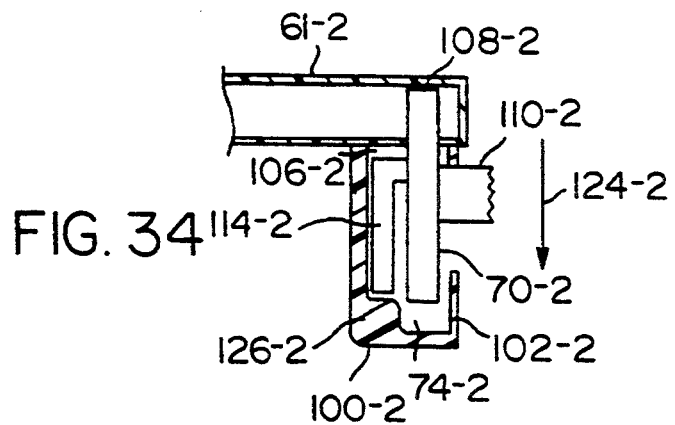
FIG. 34 is a cross-sectional view of the introducer of FIG. 26.

Operation of valve 70-2 will now be described with reference to FIG. 34. In FIG. 34, valve 70-2 is shown in a 'closed' position, such that forward end 108-2 extends through notch 104-2 and is held in contact against the inner wall of sheath 61-2, thereby sealing sheath 61-2. Spring element 114-2 biases valve 70-2 into the position depicted in FIG. 34, so that sheath 61-2 is normally sealed. Upon application of force on ridged protrusion 110-2 in the direction of arrow 124-2, spring element 114-2 is compressed against a back wall 126-2 of well 106-2, such that forward end 108-2 of valve 70-2 is retracted out of sheath 61-2, thereby leaving sheath 61-2 open and unobstructed. When force on protrusion 110-2 is removed, spring element 114-2 decompresses, restoring valve 70-2 to its closed position and resealing sheath 61-2.

Figure 35:
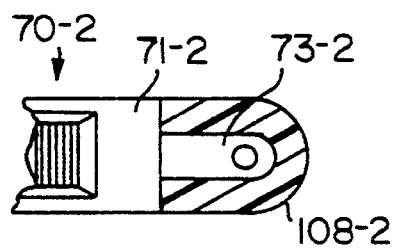
FIG. 35 is a top view of an alternative embodiment of the valve from the introducer of FIG. 26.
Figure 36:
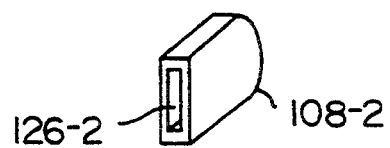
FIG. 36 is a perspective view of the alternative embodiment of the valve from the introducer of FIG. 26.

In the foregoing description of the present embodiment of the invention, it has been assumed that the components are made of relatively rigid material, such as polyethylene or the like. It is contemplated by the inventors, however, that a better seal may be achieved between the forward end 108-2 of valve 70-2 and the inner wall of cylindrical sheath 61-2 if valve 70-2 had a composite construction as depicted in FIGS. 35 and 36. In particular, it is contemplated that valve 70-2 may comprise a first, rigid valve body 71-2 having a rigid forward protrusion 73-2 extending therefrom, around which a more resilient (e.g., silicone rubber or the like) end piece 108-2 may be fitted. End piece 108-2 may be molded as shown in FIG. 36 with a cavity 126-2 therein for engaging rigid protrusion 73-2 on valve body 71-2.

Figure 37:
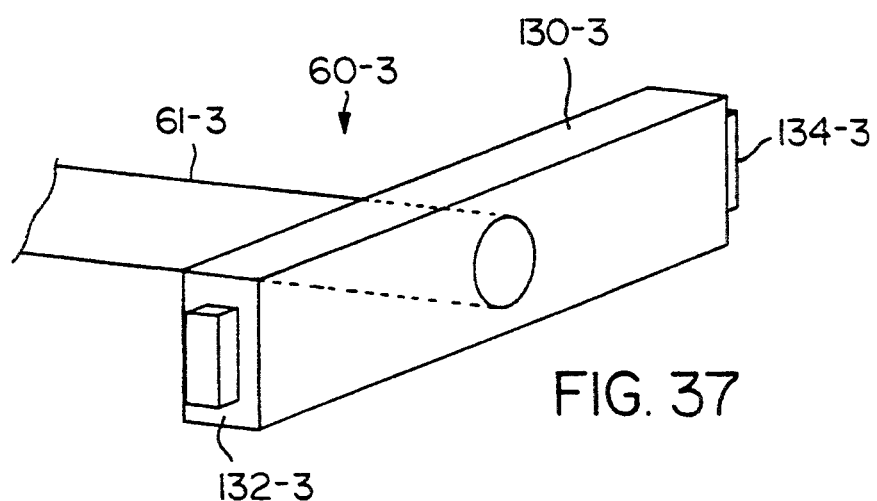
FIG. 37 is a perspective view of an introducer in accordance with another embodiment of the present invention.
Figure 38:
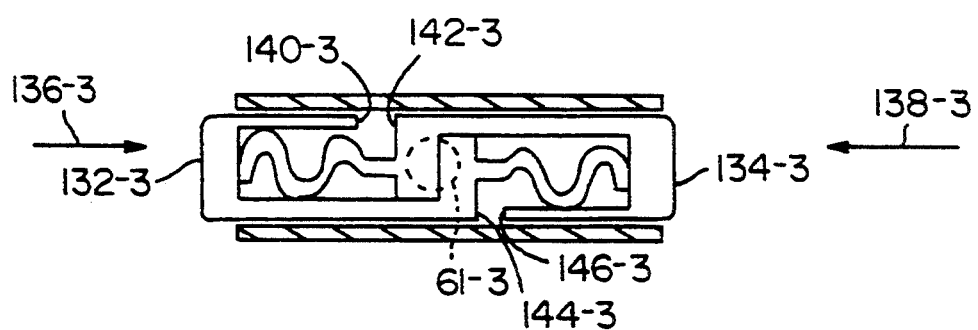
FIG. 38 is a cross-sectional view of the introducer of FIG. 37.

Yet another embodiment of the present invention, depicted in FIGS. 37 and 38, is contemplated by the inventors. It is believed that the embodiment of FIGS. 37 and 38 is best suited for non-splittable introducer sheaths. As shown in FIG. 37, introducer 60-3 comprises a unitary endpiece 130-3 disposed at the distal end of a cylindrical sheath body 61-3. Endpiece 130-3 has compression elements 132-3 and 134-3 extending outward from its ends. Introducer 60-3, like introducer 60-2 previously described with reference to FIGS. 26 through 36, is biased to a normally 'closed' or sealed condition; 'opening' or unsealing sheath 61-3 in the embodiment of FIG. 37 is accomplished by grasping endpiece 130-3, as between the thumb and forefinger, such that Operation of the compression elements of FIG. 37 will be best appreciated with reference to FIG. 38, wherein compression elements 132-3 and 134-3 are shown to be identical, oppositely-oriented and interlocking. In the state shown in FIG. 38, the circular end of sheath 61-3 is completely obstructed half by compression element 132-3 and half by compression element 134-3. When force is simultaneously applied in the directions of arrows 136-3 and 138-3, compression element 134-3 is compressed against compression element 132-3, and element 132-3 is compressed against element 134-3, thereby exposing the end of sheath 61-3. The extent to which compression elements 132-3 and 134-3 is mutually determined by the two elements coming in contact with each other. In particular, as shown in FIG. 38, the point of element 132-3 designated as 140-3 will contact element 134-3 at the point designated 142-3; likewise, the point on element 134-3 designated 146-3 will contact point 144-3 of element 132-3.

From the foregoing detailed description of specific embodiments of the invention, it should be apparent that means for restricting the flow of blood and air through a transvenous lead introducer sheath have been disclosed. While particular embodiments of the invention have been described herein in some detail, this has been done for the purposes of illustration only, and is not intended to be taken as limiting the scope of the present invention as defined in the appended claims. It is contemplated by the inventors that various alterations, substitutions, and modifications may be made to the disclosed embodiments of the invention without departing from the spirit and scope of the present invention, as defined in the claims.

What is claimed is:

1. An introducer for introducing a lead or catheter comprising:
   an introducer sheath having a hollow cylindrical body configured to permit the introduction of a lead or catheter therethrough, said sheath open at its proximal and distal ends;
   a tab disposed at the proximal end of said introducer sheath, extending radially outward therefrom;
   sliding valve means disposed on said tab, said sliding valve means adapted to slide from a first, open position wherein a forward end of said sliding valve means is disposed over said tab, to a second, closed position wherein said forward end of said sliding valve means is disposed over said open proximal end of said introducer sheath;
   such that said sliding valve means, in said closed position, substantially prevents the passage of air and blood through said introducer sheath; and
   means for permitting removal of said introducer from said lead or catheter without requiring said introducer to be removed over an end of said lead or catheter.

2. An introducer in accordance with claim 1 wherein said means for permitting removal of said introducer from said lead or catheter without requiring said introducer to be removed over an end of said lead or catheter comprises a score line within said introducer sheath.

3. An introducer in accordance with claim 1, wherein said sliding valve means comprises a valve element spring-biased to assume a normally closed position by a spring element coupled to said valve element.

4. An introducer system for introducing a lead or catheter into a body comprising:
   an introducer sheath having a hollow body configured to permit the introduction of a lead or catheter therethrough, said introducer sheath open at its proximal and distal ends;
   a member disposed at the proximal end of said introducer sheath, extending radially outward therefrom;
   sliding valve means disposed on said member, said sliding valve means adapted to slide from a first, open position wherein a forward end of said sliding valve means is disposed over said member, to a second, closed position wherein said forward end is disposed over said open proximal end of said introducer sheath such that said sliding valve means, in said closed position, substantially prevents the passage of air and blood through said sheath;
   means for permitting removal of said introducer sheath and said sliding valve means from said lead or catheter without requiring said introducer sheath and said sliding valve means to be removed over an end of said lead or catheter; and
   a dilator removably inserted in said introducer sheath, having a conically tapered end and a flared endpiece adapted to facilitate insertion of a guidewire into said dilator, said dilator being adapted to be inserted, tapered end first, into the proximal end of said introducer sheath, such that said flared endpiece is brought into contact with said member.

5. An introducer system in accordance with claim 4 wherein said means for permitting removal of said introducer sheath and said sliding valve means from said lead or catheter without requiring said introducer sheath and said sliding valve means to be removed over an end of said lead or catheter comprise a splittable line on said sheath.

6. An introducer system in accordance with claim 5 wherein said means for permitting removal of said introducer sheath and said sliding valve means from said lead or catheter comprise a sheath slitter.

7. An introducer system for introducing a lead or catheter into a body comprising:

a longitudinally separable introducer sheath having a proximal end and a distal end, said introducer sheath further having a lumen extending therethrough, said lumen configured to permit a lead or catheter to be positioned therethrough;

separable valve means positioned on said proximal end of said introducer sheath, said valve means adapted to slide from a first, open position wherein said valve means is disposed away from said lumen, to a second, closed position wherein said valve means is disposed over said lumen such that said valve means, in said closed position, substantially prevents the passage of air and blood through said introducer sheath; and a vessel dilator removably inserted in said introducer sheath, said dilator having a hollow body, said dilator having a first end and a second end, said first end being tapered and having an endpiece and adapted to facilitate insertion of a guidewire into said dilator, said dilator being adapted to be inserted, said first end first, into said proximal end of said introducer sheath.

8. An introducer system in accordance with claim 7 wherein said introducer sheath further comprises means for permitting removal of said introducer sheath from said lead or catheter without requiring said introducer sheath to be removed over an end of said lead or catheter.

9. An introducer system for introducing a lead or catheter comprising:

an introducer sheath having a hollow cylindrical body, said sheath open at its proximal and distal ends;

a tab disposed at the proximal end of said introducer sheath;

a sliding valve member disposed on said tab, said sliding valve member slidable from a first position, wherein a forward end of said sliding valve member is disposed over said tab, to a second position, wherein said forward end of said sliding valve member is disposed over said open proximal end of said introducer sheath; and means for permitting removal of said introducer system from said lead or catheter without requiring said introducer system to be removed over an end of said lead or catheter.

10. An introducer system in accordance with claim 9 further comprising a vessel dilator disposed through said introducer sheath, having a hollow body, a conically tapered end and a flared endpiece.

11. An introducer system in accordance with claim 9 wherein said means for permitting removal of said introducer system from said lead or catheter without requiring said introducer system to be removed over an end of said lead or catheter comprises a score line within said introducer sheath.

12. An introducer system in accordance with claim 9 wherein a guidewire is disposed through said introducer sheath and wherein the forward end of the sliding valve member has a notch formed therein, adapted to engage the guidewire therein when the sliding valve member is slid to the second position before the guidewire is removed from the introducer sheath, such that passage of air and blood through the introducer sheath is substantially prevented.

13. An introducer system in accordance with claim 9 wherein the means for permitting removal of the introducer system from the lead or catheter comprise a splittable tab.

14. An introducer system in accordance with claim 9 wherein the means for permitting removal of the introducer system from the lead or catheter comprise a sheath slitter.

15. An introducer system for introducing a lead or catheter into a body comprising:

a longitudinally separable introducer sheath having a proximal end and a distal end, said introducer sheath further having a lumen extending therethrough, said lumen configured to permit a lead or catheter to be positioned therethrough; and longitudinally separable valve means positioned on said proximal end of said introducer sheath, said valve means adapted to slide from a first, open position wherein said valve means is disposed away from said lumen, to a second, closed position wherein said valve means is disposed over said lumen such that said valve means, in said closed position, substantially prevents the passage of air and blood through said introducer sheath.

16. An introducer system in accordance with claim 15 further comprising a vessel dilator removably inserted in said introducer sheath, said dilator having a hollow body, said dilator having a first end and a second end, said first end being tapered and having an endpiece and adapted to facilitate insertion of a guidewire into said dilator, said dilator being adapted to be inserted, said first end first, into said proximal end of said introducer sheath.

* * * * *